(12) United States Patent
Hall et al.

(10) Patent No.: US 6,387,663 B1
(45) Date of Patent: May 14, 2002

(54) TARGETING PHARMACEUTICAL AGENTS TO INJURED TISSUES

(75) Inventors: Frederick L. Hall; Erlinda M. Gordon, both of Glendale; Vaughn A. Starnes, Pasadena; W. French Anderson, San Marino, all of CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/127,134

(22) Filed: Jul. 31, 1998

(51) Int. Cl.⁷ .................................................. C12P 21/04
(52) U.S. Cl. ..................... 435/69.7; 435/69.1; 435/4; 435/366; 435/395; 435/174; 435/180; 435/252.3; 424/520; 424/93.7; 424/9.4; 424/1.69; 530/350; 530/402
(58) Field of Search ................. 424/520, 93.7, 424/9.4, 1.69; 435/366, 395, 69.7, 174, 180, 4, 69.1, 252.3; 530/402, 350

(56) References Cited

U.S. PATENT DOCUMENTS 5,800,811 A  *  9/1998  Hall et al. ................. 424/93.7

FOREIGN PATENT DOCUMENTS

| WO | WO 96/39430 | * 12/1996 |
| WO | WO 98/44938 | * 10/1998 |
| WO | WO 98/51700 | * 11/1998 |

OTHER PUBLICATIONS

Klagsbrun et al., Annual Review of Physiology, vol. 53, pp. 217–239, 1991.*

Takagi et al., Biochemistry, vol. 31, pp. 8530–8534, 1992.*

Magovern et al., "Regional Angiogenesis Induced in Nonischemic Tissue by an Adenoviral Vector Expressing Vascular Endothelial Growth Factor," *Human Gene Therapy*, 8:215–227 (Jan. 20, 1997).

Nishi, N. et al., "Collagen–binding growth factors; Production and characterization of functional fusion proteins having a collagen–binding domain", Jun. 1998, Proc. Natl. Acad. Sci. USA, vol. 95, pp. 7018–7023.

Gordon, E.M. et al., "Capture and expansion of bone marrow–derived mesenchymal progenitor cells with a transforming growth factor–β1–von Willebrand's factor fusion protein for retrovirus–mediated delivery of coagulation factor IX", Jul. 20, 1997, Human Gene Therapy, vol. 8, pp. 1385–1394.

Sadler, J.E. et al., "Cloning and characterization of two cDNAs coding for human von Willebrand factor", Oct. 1985, Natl. Acad. Sci. USA, vol. 82, pp. 6394–6398.

* cited by examiner

Primary Examiner—Christopher S. F. Low
Assistant Examiner—Hope A. Robinson
(74) Attorney, Agent, or Firm—Fish & Richardson P.C.

(57) ABSTRACT

The present invention provides new compositions and methods to induce therapeutic angiogenesis locally utilizing a collagen binding domain to target an angiogenesis modulating agents. Fusion polypeptides containing a collagen binding domain linked to an angiogenesis modulating agent are provided, as are nucleic acid sequences encoding the fusion polypeptides. Also included are methods for locally altering circulation by administering a fusion polypeptide consisting of a collagen binding domain linked to an angiogenesis modulating agent, or by administering a nucleic acid sequences encoding the fusion polypeptide. Tissue grafts in which isolated tissue is treated with a fusion polypeptide consisting of a collagen binding domain linked to an angiogenesis modulating agent, or with a nucleic acid sequences encoding the fusion polypeptide are also provided, as are methods of making the grafts.

4 Claims, 7 Drawing Sheets

ENDOTHELIAL CELL TRAPPING IN SYNTHETIC VASCULAR GRAFTS

1. GELATIN COATING OF THE GRAFT

PBS  GEL  PBS  DRY

2. ADDITION OF THE TARGETED GROWTH FACTOR

PBS  C-VEGF  PBS  D-10

3. TESTING OF THE FORTIFIED GRAFT

IN VITRO   IN VIVO

SEQUENCE LISTING

```
<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: Description of Artificial  Sequence: Artificial
      Decapeptide sequence

<400> SEQUENCE: 1

Trp Arg Glu Pro Ser Phe Met Ala Leu Ser
  1               5                  10

<210> SEQ ID NO 2
<211> LENGTH: 28
<212> TYPE: DNA
<213> ORGANISM: Artificial Sequence
<220> FEATURE:
<223> OTHER INFORMATION: Description of Artificial  Sequence: Artifical
      Sense Primer

<400> SEQUENCE: 2
```

```
                                                  -continued catatgggtg cacccatggc agaaggag                                        28

<210> SEQ ID NO 3
<211> LENGTH: 27
<212> TYPE: DNA
<213> ORGANISM: Artificial Sequence
<220> FEATURE:
<223> OTHER INFORMATION: Description of Artificial  Sequence: Artificial
      Antisense Primer

<400> SEQUENCE: 3
tcatctatct ttctttggtc tgcattc                                         27

<210> SEQ ID NO 4
<211> LENGTH: 30
<212> TYPE: DNA
<213> ORGANISM: Artificial Sequence
<220> FEATURE:
<223> OTHER INFORMATION: Description of Artificial  Sequence: Artificial
      Sense Primer

<400> SEQUENCE: 4
catatgtggc gcgaaccgag cttcatggct                                      30

<210> SEQ ID NO 5
<211> LENGTH: 28
<212> TYPE: DNA
<213> ORGANISM: Artificial Sequence
<220> FEATURE:
<223> OTHER INFORMATION: Description of Artificial  Sequence: Artificial
      Sense Primer

<400> SEQUENCE: 5
ctgagcggtg cacccatggc agaaggag                                        28

<210> SEQ ID NO 6
<211> LENGTH: 27
<212> TYPE: DNA
<213> ORGANISM: Artificial Sequence
<220> FEATURE:
<223> OTHER INFORMATION: Description of Artificial  Sequence: Artificial
      Antisense Primer

<400> SEQUENCE: 6
tcatctatct ttctttggtc tgcattc                                         27

<210> SEQ ID NO 7
<211> LENGTH: 24
<212> TYPE: DNA
<213> ORGANISM: Artificial Sequence
<220> FEATURE:
<223> OTHER INFORMATION: Description of Artificial  Sequence: Artificial
      Antisense Primer

<400> SEQUENCE: 7
tcaccgcctc ggcttgtcac atca                                            24
```

US 6,387,663 B1

TARGETING PHARMACEUTICAL AGENTS TO INJURED TISSUES

FIELD OF THE INVENTION

The present invention relates to the targeting of pharmaceutical agents, more specifically to the use of collagen binding domains to target pharmaceutical agents to a desired tissue.

BACKGROUND OF THE INVENTION

Ischemic coronary artery disease is one of the leading causes of morbidity and mortality in the United States. Current therapeutic approaches include risk factor modification, reduction of myocardial oxygen demand, and localized restoration of flow to the coronary arterial system by means of angioplasty, stents, or coronary bypass. These treatment options are often insufficient and a significant number of patients are not even candidates for the surgical options. Some attempts have been made to improve coronary flow blood supply to ischemic myocardium by grafting or by measures to enlarge existing blood vessels.

Therapeutic angiogenesis is a process which can be used to develop collateral blood vessels to the myocardium. The term "angiogenesis" refers to a process of tissue vascularization that involves the development of new vessels. Angiogenesis is a complex process involving the breakdown of extracellular matrix, with proliferation and migration of endothelial and smooth muscle cells ultimately resulting in the formation and organization of new blood vessels (Folkman, J., and Klagsbrun, M., Science 235:442–7, 1987). Angiogenesis typically occurs via one of three mechanisms: (1) neovascularization, where endothelial cells migrate out of pre-existing vessels beginning the formation of the new vessels; (2) vasculogenesis, where the vessels arise from precursor cells de novo; or (3) vascular expansion, where existing small vessels enlarge in diameter to form larger vessels (Blood, C. H., and Zetter, B. R., Biochem. Biophys. Acta. 1032:89–118, 1990). Angiogenesis is an important process in normal processes of neonatal growth and in the female reproductive system during the corpus luteum growth cycle (see Moses, M. A., et al., Science 248: 1408–10, 1990). Under normal conditions, all processes involving the new formation or the remodeling of existing or new blood vessels is a self-limiting process, and the expansion of the specific cell types is controlled and concerted. Angiogenesis is also involved in wound healing and in the pathogenesis of a large number of clinical diseases including tissue inflammation, arthritis, asthma, tumor growth, diabetic retinopathy, and other conditions. Clinical manifestations associated with angiogenesis are referred to as angiogenic diseases (Folkman and Klagsbrun, 1987, supra).

The term "growth factors" originally referred to substances that promote cell growth. It is used to indicate molecules that function as growth simulators (mitogens) but also as growth inhibitors (sometimes referred to as negative growth factors ). Growth factors are also known to stimulate cell migration (e.g., mitogenic cytokines ), function as chemotactic agents, inhibit cell migration or invasion of tumor cells, modulate differentiated functions of cells, be involved in apoptosis and promote survival of cells. Such factors can be secreted as diffusible factors and can also exist in membrane-anchored forms. They can, therefore, act in an autocrine, paracrine, juxtacrine or retrocrine manner. A cytokine is one type of growth factor.

The term "cytokine" is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Cytokines comprise interleukins, initially thought to be produced exclusively by leukocytes; lymphokines, initially thought to be produced exclusively by lymphocytes; monokines, initially thought to be produced exclusively by monocytes; interferons, initially thought to be involved in antiviral responses; colony stimulating factors, initially thought to support the growth of cells in semisolid media; and chemokines, thought to be involved in chemotaxis, and a variety of other proteins. In vivo, the expression of most cytokines is strictly regulated; these factors are usually produced only by activated cells in response to an induction signal.

In general, cytokines act on a wider spectrum of target cells than hormones. Perhaps the major feature distinguishing cytokines from mediators regarded generally as hormones is the fact that, unlike hormones, cytokines are not produced by specialized cells which are organized in specialized glands; there is not a single organ source for these mediators. The fact that cytokines are secreted proteins also means that the sites of their expression does not necessarily predict the sites at which they exert their biological function. Some cytokines have been found, upon determination of their primary structures, to be identical with classical enzymes (for example: adult T-cell leukemia-derived factor (ADF), nm23, platelet-derived endothelial cell growth factor (PD-ECGF, or neuroleukin). Cytokines normally do not possess enzymatic activities although there is a growing list of exceptions. The biological activities of cytokines can be measured by a variety of bioassays employing, among other things, factor-dependent cell lines, or cytokines can be measured by other assays using, for example, antibodies. Message amplification phenotyping employs modem techniques of molecular biology and detects the presence of cytokine-specific mRNAs.

Many experiments have suggested that tissues can produce angiogenic factors which promote angiogenesis under conditions of poor blood supply during both normal and pathological conditions. Several angiogenic factors have been demonstrated in vivo to promote angiogenesis in the ischemic myocardium, including basic fibroblast growth factor (bFGF), and vascular endothelial growth factor (VEGF), amongst cytokines and other molecules (Lopez and Simons, Drug Delivery 3:143, 1996). These factors and compounds differ in cell specificity and in the mechanisms by which they induce the growth of new blood vessels. For example, they may induce the migration and proliferation of endothelial cells or stimulate the production collagenase (see Klagsbrun, M., and D'Amore, P. A., Ann. Rev. Physiol. 53:217–39, 1991). There are a number of bioassays which allow direct determination of angiogenic activities (Wilting, J., et al., Anat. Embrol. (Berl) 183:259–71, 1991).

Vascular endothelial growth factor (VEGF) is a homodimeric, heavily glycosylated protein of 46–48 kDa (24 kDa subunits) (for review see Ferrara, N., et al., J. Cell Bio. 47:211, 1991; Ferrara, N., et al., Endocrin. Rev. 13:18–32, 1991). Glycosylation is not required, however, for biological activity. The subunits are linked by disulphide bonds. The human factor occurs in several molecular variants of 121, 165, 189, and 206 amino acids, arising by alternative splicing of the mRNA. Several other variants of VEGF have been described, including VEGF-B, VEGF-C, and VEGF-D. The 189 amino acid variant of VEGF (VEGF- 189) is identical with vascular permeability factor (VPF). VEGF-121 and VEGF-165 are soluble secreted forms of the factor while VEGF-189 and VEGF-206 are mostly bound to heparin-containing proteoglycans in the cell surface or in the basement membrane. Rat and bovine VEGF are one amino acid shorter than the human factor, and the bovine and human sequences show a homology of 95%. The positions of all eight cysteine residues are conserved in VEGF and PDGF. A high-affinity glycoprotein receptor for VEGF of 170–235 kDa is expressed on vascular endothelial cells. VEGF significantly influences vascular permeability and is a strong angiogenic protein in several bioassays, and has been shown to be a highly specific mitogen for vascular endothelial cells. In vitro, the two shorter forms of VEGF stimulate the proliferation of macrovascular endothelial cells, but does not appear to enhance the proliferation of other cell types.

Perivascular delivery of bFGF has been shown to improve collateral circulation and myocardial function in chronic myocardial ischemia (Harada et al., *J. Clin. Invest.* 94:623–30, 1994). Both bFGF and VEGF have been shown to enhance collateral blood flow during perivascular delivery by myocardial perfusion by heparin alginate microspheres and implantable osmotic pumps (Lopez and Simmons, 1996, supra). However, the systemic delivery of growth factors by means such as intravenous infusion has a number of limitations. A number of adverse effects have been described with the systemic administration of angiogenic growth factors, including renal and hematopoietic end-organ damage such as membranous nephropathy and bone marrow suppression as well as hemodynamic effects (Lopez and Simmons, 1996, supra). In addition, concerns have been raised as to the potential of systemic delivery of these agents to stimulate dormant neoplasias. The cost of the systemic delivery of recombinant growth factor proteins is also thought to be prohibitive.

SUMMARY OF THE INVENTION

The present invent ion provides new compositions and methods to induce therapeutic angiogenesis locally, aimed at developing new collateral blood vessels to the myocardium at risk in order to achieve localized restoration of blood flow. The present invention also provides new compositions and methods useful in a large number of clinical diseases including stroke, tissue inflammation, ulcerative conditions, arthritis, asthma, tumor growth, diabetic retinopathy, and other conditions.

In one embodiment, a fusion polypeptide including a collagen binding domain and an angiogenesis modulating agent, that is capable of binding to collagen, is provided. A nucleic acid sequence encoding a fusion polypeptide containing a collagen binding domain and an angiogenesis modulating agent, that is capable of binding to collagen, is also provided.

In another embodiment, a method for locally altering circulation in a subject by administering a circulatory modulating amount of a fusion polypeptide containing a collagen binding domain linked to an angiogenesis modulating agent to the subject, is provided. A method for locally altering circulation in a subject, by administering to the subject a therapeutically effective amount of a nucleic acid sequence encoding a fusion polypeptide containing a collagen binding domain linked to an angiogenesis modulating agent is also provided.

In a further embodiment, a tissue graft, including isolated tissue containing endothelial cells contacted with a fusion polypeptide containing a collagen binding domain linked to an angiogenesis modulating agent, is provided. A method of preparing a tissue graft by contacting isolated tissue with an effective amount of a fusion polypeptide containing a collagen binding domain linked to an angiogenesis modulating agent, is also provided. A method of activating a graft by contacting an isolated tissue with an effective amount of a nucleic acid sequence encoding a fusion polypeptide containing a collagen binding domain linked to an angiogenesis modulating agent, so that the nucleic acid sequence is expressed in said tissue, is further provided.

In yet another embodiment, a pharmaceutical composition including a fusion polypeptide containing a collagen binding domain linked to an angiogenesis modulating agent in a pharmaceutically acceptable carrier is provided. A pharmaceutical composition including a nucleic acid encoding a fusion polypeptide containing a collagen binding domain linked to an angiogenesis modulating agent in a pharmaceutically acceptable carrier is also provided.

DESCRIPTION OF THE PREFERRED EMBODIMENTS

Figure 1:
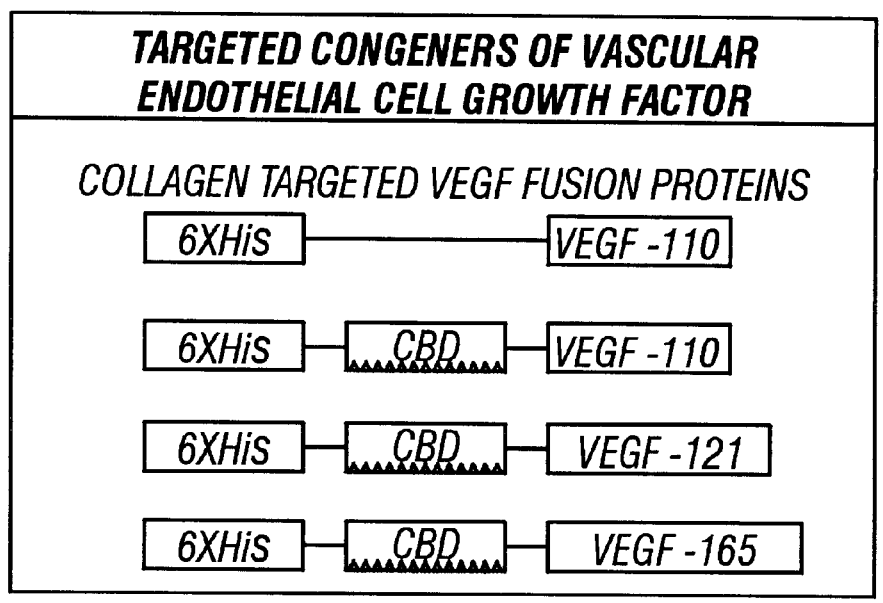
FIG. 1 is a schematic diagram of collagen targeted VEGF proteins.

It must be noted that as used herein and in the appended claims, the singular forms "a," "and," and "the" include plural referents unless the context clearly dictates otherwise. Thus, for example, reference to "a target cell" includes a plurality of such cells and reference to "the expression vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, cells and genes similar or equivalent to those described herein can be used in the practice or testing of the invention, the preferred methods, devices and materials are now described.

All publications mentioned herein are incorporated herein by reference in full for the purpose of describing and disclosing the cell lines, vectors, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The invention provides fusion polypeptides comprising a collagen binding domain and an angiogenesis modulating agent. As used in connection with the present invention the term "polypeptide" refers to a polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those which are recombinantly or synthetically synthesized. "Fragments" are a portion of a polypeptide. The term "fragment" refers to a portion of a polypeptide which exhibits at least one useful epitope. The term "functional fragments of a polypeptide," refers to all fragments of a polypeptide that retain an activity of the polypeptide. For example, a functional fragment of an angiogenesis modulating agent includes a fragment which retains angiogenic activity. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen.

Fragments can have the same or substantially the same amino acid sequence as the naturally occurring protein. "Substantially the same" means that an amino acid sequence is largely, but not entirely, the same, but retains a functional activity of the sequence to which it is related. An example of a functional activity is that the fragment may bind to an antibody that also recognizes the full length polypeptide. In general two amino acid sequences are substantially the same" or "substantially homologous" if they are at least 85% identical, or if there are a conservative variations in the sequence. A computer program, such as the BLAST program (Altschul et al., 1990) can be used to compare sequence identity, and the ALOM (Klein et al., 1985) can be used in analyzing amino acid sequences for potential peripheral and membrane-spanning regions.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The fusion polypeptides of the invention are capable of binding to collagen. A "fusion protein" is a polypeptide containing portions of amino acid sequence derived from two or more different proteins, or two or more regions of the same protein that are not normally contiguous. A "collagen binding domain" is any polypeptide, or portion thereof, that can bind collagen. Several collagen binding domains are known in the art (Cruz, M. A., et al., *Interaction of the von Willebrand factor (vWF) with collagen: Localization of the primary collagen-binding site by analysis of recombinant vWFA domain polypeptides*, J. Biol. Chem., 270:10822–10827, 1995; Hoylaerts, M. F., et al., *von Willebrand factor binds to native collagen VI primarily via its A1 domain*, Biochem. J., 324:185–191, 1997; Lankhof, H., et al., *A3 domain is essential for interaction of von Willebrand factor with collagen type III*, Thrombos Haemostas, 75;950–958, 1996. In one embodiment, the collagen binding domain is the collagen binding domain of von Willebrand factor, which is involved in the recognition of exposed vascular collagen (Takagi, J., et al., *Biochemistry* 32:8530–4, 1992; Tuan, T. L., et al., *Conn. Tiss. Res.* 34:1–9, 1996; Gordon, E. M., et al., *Hum. Gene Ther.* 8:1385–1394, all herein incorporated by reference). von Willebrand factor was initially identified as a hemostatic factor in studies of inherited hemophilias (Wagner, *Ann. Rev. Cell. Biol.* 6:217, 1990), and has been shown to perform a vital surveillance function by targeting platelet aggregates to vascular lesions (Ginsburg and Bowie, *Blood* 79:2507–2519, 1992). The decapeptide WREPSFMALS (SEQ ID NO: 1) has been identified to be key in the binding of von Willebrand's factor to collagen (Takagi, J., et al., supra, 1992; Tuan, T. L. et al., supra, 1996). Assays to identify collagen binding domains of use in the subject invention are known in the art (Takagi, J., et al., supra, 1992; Tuan, T. L. et al., supra, 1996).

An example of a method for identifying collagen binding domains is ELISA (Hall et al., Hum. Gene. Ther., 8:2183–2192, 1997. To assess the collagen binding property of the chimeric envelope protein, a recombinant envelope construct (SU-ECB-CEE+) was prepared by PCR and expressed in *E. Coli*. Approximately 1 µg of the protein was applied to collagen-coated microtiter plates and allowed to bind for 20 minutes, followed by washing under the specified conditions and detection of the bound protein by modified ELISA. In five determinations, the immunoreactive chimeric protein, SU-ECB-CEE+, remained bound to collagen after washing with PBS, 1M NaCl, 1 and 2M urea, requiring ≦3M urea to release the protein from the collagen matrices (Lanes 5–8). Collagen-coated microtiter plates and cryostat sections of treated or untreated, injured or non-injured aortic or IVC segments were incubated for 4 hours at RT at a primary antibody dilution of 1:1000. A biotinylated goat antibody to rat IgG was then applied followed by a strepavidin-horse radish peroxidase conjugate. Diaminobenzidine (DAB) was used as a chromogen followed by nickel chloride enhancement for microtiter plates. Histological slides were counterstained with hematoxylin.

An "angiogenesis modulating agent" is any agent that can induce angiogenesis or the proliferation of endothelial cells. For example, an angiogenesis modulating agent includes a cytokine, a growth factor, an enzyme, an enzymatic inhibitor, or an antibody. A "cytokine" is polypeptide which acts as a humoral regulator at nano- to picomolar concentrations and which, either under normal or pathological conditions, can modulate the functional activities of individual cells and tissues. A cytokine can mediate interactions between cells directly and/or can regulate processes taking place in the extracellular environment. Cytokines comprise interleukins, lymphokines, monokines, interferons, colony stimulating factors, and chemokines, in addition to a variety of other proteins.

One class of angiogenesis modulating agents are polypeptide angiogenic factors, such as cytokines and growth factors, which includes, but is not limited to, angiopoeitin-1, epidermal growth factor (EGF), hepatocyte growth factor (HGF), tumor necrosis factor (TNF-alpha), platelet derived endothelial cell growth factor (PD-ECGF), platelet derived growth factor (PDGF), insulin-like growth factor (IGF), interleukin-8, growth hormone, angiopoietin, vascular endothelial growth factor (VEGF), acidic and basic fibroblast growth factors (FGFs), transforming growth factor alpha (TGF-α), CYR 61 (Babic et al., Proc. Natl. Acad. Sci. USA, 95:6355, 1998; Kireeva et al., Mol. Cell. Biol. 16:1326, 1996) and platelet-derived growth factor (PDGF). Each of these molecules has been shown to induce angiogenesis in vivo. Other similar molecules that display angiogenic activity are the heparin binding growth factors (HBGFs). Other angiogenesis modulating agents have been described in addition to polypeptide angiogenic factors. For example, prostaglandins $E_1$ and $E_2$, which are lipid-derived angiogenic factors, are well known inflammatory cell attractants with angiogenic properties (*J. Natl. Cancer Inst*. 69, 475–482, 1982). In addition, nicotinamide causes an angiogenic response when tested in chick cornea or in a chick CAM assay (*Science* 236, 843–845, 1987). In addition, negative angiogenic regulatory molecules include angiostatin (O'Reilly et al., Cell 79:315, 1994); endo-statin (O'Reilly et al., Cell. 88:277, 1997); and thrombospondin (Good et al., Proc. Natl. Acad. Sci. USA, 87:6624, 1990).

The invention provides isolated nucleic acid sequences which encode a fusion polypeptide containing a collagen binding domain linked to a angiogenesis modulating agent, or a functional fragment thereof. "Polynucleotide" or "nucleic acid sequence" refers to a polymeric form of nucleotides at least 10 bases in length. By isolated nucleic acid sequence" is meant a polynucleotide that is not immediately contiguous with both of the coding sequence with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double stranded forms of DNA.

Nucleic acid sequences which encode a collagen binding domain linked to a angiogenesis modulating agent, or functional fragment thereof, can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (ie., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the nucleic acid sequences encoding the fusion polypeptide of the invention may be inserted into a recombinant expression vector. The term "recombinant expression vector" refers to a plasmid, virus or other vehicle known in the art that has been manipulated by insertion or incorporation of the nucleic acid sequences encoding the fusion peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem*. 263:3521, 1988), baculovirus-derived vectors for expression in insect cells, cauliflower mosaic virus, CaMV; tobacco mosaic virus, TMV.

Depending on the vector utilized, any of a number of suitable transcription and translation elements, including constitutive and inducible promoters, transcription enhancer elements, transcription terminators, etc. may be used in the expression vector (see, e.g., Bitter, et al., *Methods in Enzymology* 153:516–544, 1987). These elements are well known to one of skill in the art.

In yeast, a number of vectors containing constitutive or inducible promoters may be used. (For a review see, *Current Protocols in Molecular Biology*, Vol. 2, Ed. Ausubel, et al., Greene Publish. Assoc. & Wiley Interscience, Ch. 13, 1988; Grant, et al., "Expression and Secretion Vectors for Yeast," in *Methods in Enzymology*, Eds. Wu & Grossman, Acad. Press, N.Y., Vol. 153, pp.516–544, 1987; Glover, *DNA Cloning*, Vol. II, IRL Press, Wash., D.C., Ch. 3, 1986; and "Bitter, Heterologous Gene Expression in Yeast," *Methods in Enzymology*, Eds. Berger & Kimmel, Acad. Press, N.Y., Vol. 152, pp. 673–684, 1987; and *The Molecular Biology of the Yeast Saccharomyces*, Eds. Strathern et al., Cold Spring Harbor Press, Vols. I and II, 1982.) A constitutive yeast promoter such as ADH or LEU2 or an inducible promoter such as GAL may be used ("Cloning in Yeast," Ch. 3, R. Rothstein In: *DNA Cloning* Vol.11, A Practical Approach, Ed. D M Glover, IRL Press, Wash., D.C., 1986). Alternatively, vectors may be used which promote integration of foreign DNA sequences into the yeast chromosome.

By "transformation" is meant a permanent genetic change induce in a cell following incorporation of new DNA (i.e., DNA exogenous to the cell). Where the cell is a mammalian cell, the permanent genetic change is generally achieved by introduction of the DNA into the genome of the cell. By "transformed cell" is meant a cell into which (or into an ancestor of which has been introduced, by means of recombinant DNA techniques, a DNA molecule encoding a fusion protein consisting of a collagen binding domain linked to an angiogenesis modulating agent, or fragment thereof. Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

A fusion polypeptide of the invention can be produced by expression of nucleic acid encoding the protein in prokaryotes. These include but are not limited to microorganisms such as bacteria transformed with recombinant bacteriophage DNA, plasmid DNA or cosmid DNA expression vectors encoding a fusion protein of the invention. The constructs can be expressed in E. Coli in large scale for in vitro assays. Purification from bacteria is simplified when the sequences include tags for one-step purification by nickel-chelate chromatography. The construct can also contain a tag to simplify isolation of the fusion polypeptide. For example, a polyhistidine tag of, e.g., six histidine residues, can be incorporated at the amino terminal end of the fluorescent protein. The polyhistidine tag allows convenient isolation of the protein in a single step by nickel-chelate chromatography. The fusion polypeptide of the invention can also be engineered to contain a cleavage site to aid in protein recovery. Alternatively, the fusion polypeptides of the invention can be expressed directly in a desired host cell for assays in situ.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and WI38.

For long-term, high-yield production of recombinant proteins, stable expression is preferred. Rather than using expression vectors which contain viral origins of replication, host cells can be transformed with the cDNA encoding a fusion protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11:223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22:817, 1980) genes can be employed in tk⁻, hgprt⁻ or aprt⁻ cells respectively. Also, antimetabolite resistance can be used as the basis of selection for dhfr, which confers resistance to methotrexate (Wigler, et al., *Proc. Natl. Acad. Sci USA*, 77:3567, 1980; O'Hare, et al, *Proc. Natl. Acad. Sci. USA*, 8:1527, 1981); gpt, which confers resistance to mycophenolic acid (Mulligan & Berg, *Proc. Natl. Acad. Sci. USA*, 78:2072, 1981; neo, which confers resistance to the aminoglycoside G-418 (Colberre-Garapin, et al.,*J. Mol. Biol.*, 150:1, 1981); and hygro, which confers resistance to hygromycin (Santerre, et al., *Gene*, 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA*, 85:8047, 1988); and ODC (omithine decarboxylase) which confers resistance to the ornithine decarboxylase inhibitor, 2-(difluoromethyl)-DL-ornithine, DFMO (McConlogue L., In: *Current Communications in Molecular Biology*, Cold Spring Harbor Laboratory, ed., 1987).

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

The present invention provides compositions and methods useful in locally altering circulation in a subject. A subject is any mammal, including mice, rats, rabbits, dogs, cats, pigs, cows, sheep, and humans. In a preferred embodiment, the subject is human. The method of the invention can be used to locally alter circulation in a subject who has a disorder that can be treated using an angiogenesis modulating agent. The terms "treatment," "treating," "treat" and the like are used herein to generally mean obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c)

relieving the disease symptom, i.e., causing regression of the disease or symptom. Disorders that can be treated using a method of the invention include, but are not limited to: cardiovascular disease, such as myocardial infarction and peripheral artery disease, post-balloon angioplasty vascular restenosis, ulcerative and inflammatory disorders, genetic defects and neoplasia (see below). In addition the method of the invention can be used to augment transmyocardial laser revascularization, to promote endothelial stem cell isolation and expansion, or to promote endothelialization of vascular grafts.

It is envisioned that the method of the invention can be used to aid wound healing. For example, the method of the invention can be used in aiding tissue repair or regeneration at an ulcer site in a human or other subject. In another aspect, the invention is useful for the purposes of promoting tissue growth during the process of tissue engineering. By "tissue engineering" is meant the creation, design, and fabrication of biological prosthetic devices, in combination with synthetic or natural materials, for the creation, augmentation, or replacement of body tissues and organs. Thus, the method can be used to augment the design and growth of tissue inside the body to repair or replace diseased or damaged tissue. A specific, non-limiting example is use the use of a method of the invention in promoting the growth of skin graft replacements which are used as a therapy in the treatment of burns and ulcers.

The term "neoplasia" refers to a disease of inappropriate cell proliferation. This derangement is most evident clinically when tumor tissue bulk compromises the function of vital organs. Concepts describing normal tissue growth are applicable to malignant tissue because normal and malignant tissues can share similar growth characteristics, both at the level of the single cell and at the level of the tissue. Tumors are as much a disease of disordered tissue growth regulation as of disordered cellular growth regulation. The growth characteristics of tumors are such that new cell production exceeds cell death; a neoplastic event tends to produce an increase in the proportion of stem cells undergoing self-renewal and a corresponding decrease in the proportion progressing to maturation (McCulloch, E. A., et al., "The contribution of blast cell properties to outcome variation in acute myeloblastic leukemia (AML), *Blood* 59:601–608, 1982).

By "locally altering circulation" is meant a change in the pattern of blood flow at a particular site in a subject. The change in the pattern of blood flow can be caused by a change in shape or morphology of one blood vessel, or by changing the pattern of vessels. One means of locally altering the circulation is by the formation of collateral blood vessels. Another means of locally altering circulation is by promoting the division of endothelial cells, or by inducing angiogenesis. The term "endothelial cells" means those cells making up the endothelium, the monolayer of simple squamous cells which lines the inner surface of the circulatory system. These cells retain a capacity for cell division, although they proliferate very slowly under normal conditions, undergoing cell division perhaps only once a year. The proliferation of endothelial cells can be demonstrated by using [$^3$H] thymidine to label cells in the S phase. In normal vessels the proportion of endothelial cells that become labeled is especially high at branch points in arteries, where turbulence and wear seem to stimulate turnover. (Goss, R. J., *The Physiology of Growth*, Academic Press, New York, pp.120–137, 1978). Normal endothelial cells are quiescent, i.e., are not dividing, and as such are distinguishable from angiogenic endothelial cells as discussed below.

Endothelial cells also have the capacity to migrate, a process important in angiogenesis. Endothelial cells form new capillaries in vivo when there is a need for them, such as during wound repair or when there is a perceived need for them as in tumor formation. The formation of new vessels is termed "angiogenesis," and involves molecules (angiogenic factors) which can be mitogenic or chemoattractant for endothelial cells (Klagsburn, supra). During angiogenesis, endothelial cells can migrate out from an existing capillary to begin the formation of a new vessel, i.e., the cells of one vessel migrate in a manner which allows for extension of that vessel (Speidel, C. C., *Am J. Anat.* 52:1–79). In vitro studies have documented both the proliferation and migration of endothelial cells; endothelial cells placed in culture can proliferate and spontaneously develop capillary tubes (Folkman, J., and Haudenschild, C., *Nature* 288:551–56, 1980).

The terms "angiogenic endothelial cells" and "endothelial cells undergoing angiogenesis" and the like are used interchangeably herein to mean endothelial cells (as defined above) undergoing angiogenesis (as defined above). Thus, angiogenic endothelial cells are endothelial cells which are proliferating at a rate far beyond the normal condition of undergoing cell division roughly once a year. The rate of differentiation from normal proliferation of endothelial cells may be 2, 5, or 10 times or more that of normal proliferation and can vary greatly depending on factors such as the age and condition of the patient, the type of tumor involved, the type of vascular disease, etc. Provided the difference in the degree of proliferation between normal endothelial cells and angiogenic endothelial cells is measurable and considered biologically significant then the two types of cells are differentiable. The term "corresponding endothelial cells" "normal or quiescent endothelial cells" and the like are used in order to refer to normal, quiescent endothelial cells contained within the same type of tissue (under normal conditions) when some of the endothelial cells are undergoing angiogenesis and some of the endothelial cells are quiescent.

A "circulatory modulating amount" is the amount of any agent which can modulate a local alteration in circulation. An "agent" is any molecule, e.g., protein, nucleic acid, or pharmaceutical, with the capability of altering local circulation. An "angiogenesis modulating agent" is any agent which can modulate angiogenesis or the proliferation of endothelial cells. The term "modulate" envisions the induction or augmentation of angiogenesis or local circulation where appropriate. Alternatively, an angiogenesis modulating agent can inhibit angiogenesis in order to locally affect circulation. For example, an angiogenesis modulating agent can be a cytokine, a growth factor, an enzyme, an enzymatic inhibitor, or an antibody.

In one embodiment, a method for locally altering circulation in a subject, by administering to the subject a fusion polypeptide comprising a collagen binding domain linked to an angiogenesis modulating agent is provided. "Administering" the pharmaceutical composition of the present invention may be accomplished by any means known to the skilled artisan.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention can be administered locally. "Local" administration is the delivery of a composition of an invention at or near to the physiological site where treatment is desired. The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science*, 249:1527–1533, 1990, which is incorporated herein by reference.

By "therapeutically effective dose" or "circulatory modulatory amount" is meant the quantity of a compound according to the invention necessary to locally alter the circulation. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, each of which is herein incorporated by reference.

The present invention also provides a method for locally altering circulation in a subject by administering a therapeutically effective amount of a nucleic acid sequence encoding a fusion polypeptide comprising a collagen binding domain linked to a angiogenesis modulating agent. Such therapy would achieve its therapeutic effect by introduction of a therapeutic polynucleotide encoding a fusion polypeptide comprising a collagen binding domain linked to an angiogenesis modulating agent into cells in vivo having the disorder or introducing the therapeutic polynucleotide into cells ex vivo and then reintroducing the cells into the subject. Delivery of the therapeutic polynucleotide can be achieved using a recombinant expression vector such as a chimeric virus or a colloidal dispersion system. Especially preferred for therapeutic delivery of polynucleotide sequences encoding a fusion polypeptide comprising a collagen binding domain linked to an angiogenesis modulating agent, is the use of targeted liposomes.

Various viral vectors which can be utilized for the introduction of nucleic acid sequences into cells as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (-MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a nucleic acid sequence encoding a fusion polypeptide of the invention into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the polynucleotide sequences encoding a fusion polypeptide comprising a collagen binding domain linked to an angiogenesis modulating agent.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In another embodiment the method provides an isolated tissue graft. The graft contains isolated tissue including endothelial cells and a fusion polypeptide comprising a collagen binding domain linked to an angiogenesis modulating agent. By "isolated tissue" is meant tissue that is removed from its natural location in a subject. In a preferred embodiment, the isolated tissue has an endothelial cell component. The tissue can be a organ, a portion of an organ, or isolated cells. For example, the tissue can be skin, several cell layer isolated from the skin, a vessel, or vascular tissue isolated from a vessel. In one aspect the graft is a vessel, for examples a vessel used for bypass grafts. These can include aortocoronary, aortoiliac, aortorenal, femoropopliteal. In another aspect the tissue can be a heart. The isolated tissue can be contacted with a an effective amount of a fusion polypeptide comprising a collagen binding domain linked to an angiogenesis modulating agent in vitro, prior to implantation in the same or a different subject. "Contacting" includes conditions which allows interaction between the tissue and and a fusion polypeptide comprising a collagen binding domain linked to an angiogenesis modulating agent, and includes in solution and solid phase.

The invention further provides method of preparing a tissue graft by contacting isolated tissue with an effective amount of a fusion polypeptide comprising a collagen binding domain linked to an angiogenesis modulating agent. The isolated tissue can be autologous or heterologous tissue. An "activated" graft is isolated tissue which has been stimulated such that angiogenesis is induced in vitro, or in which angiogenesis can occur once the graft is placed into a recipient. An "allograft" is a graft to be transplanted into a genetically different member of the same species. A "xenograft" is a graft from a member of one species to be transplanted into a member of a different species. The term "donor" refers to a subject or culture from whom a tissue is taken; the term "recipient" refers to a subject or culture in whom the tissue is to be placed. The recipient may be treated with an immunosuppressive agent before or after transplantation.

The isolated tissue can be contacted with an effective amount of a fusion polypeptide comprising a collagen binding domain linked to an angiogenesis modulating agent in vitro, prior to implantation in the same or a different subject. Alternatively the isolated tissue may be implanted into a similar location in a second subject, or implanted to a different location in the same subject, and contacted after implantation with a fusion polypeptide comprising a collagen binding domain linked to an angiogenesis modulating agent in vivo.

Alternatively, the isolated tissue can be contacted with an effective amount of a nucleic acid sequence encoding a fusion polypeptide comprising a collagen binding domain linked to an angiogenesis modulating agent. The isolated tissue can be contacted with a an effective amount of nucleic acid sequence encoding a fusion polypeptide comprising a collagen binding domain linked to an angiogenesis modulating agent in vitro, prior to implantation in the same or a different subject. Alternatively the isolated tissue may be implanted into a similar location in a second subject, or implanted to a different location in the same subject, and contacted after implantation with a nucleic acid sequence encoding a fusion polypeptide comprising a collagen binding domain linked to an angiogenesis modulating agent in vivo. Contacting can occur either in vivo or in vitro, and includes conditions which allow uptake and expression of the nucleic acid sequence encoding a fusion polypeptide of the invention.

While not required, it may be desirable to administer an immunosuppressive agent to a recipient of the graft prior to transplantation and/or after transplantation. An agent such as Cyclosporine A (CsA) is preferably used, however other agents which cause immune suppression, such as rapamycin, desoxyspergualine, and FK506 or functional equivalents of these compounds, may also be utilized. CsA is preferably administered by injection at an immunosuppressive dose. The duration of CsA treatment may range from about 2 to about 20 days.

If utilized, the immunosuppressive agent is administered by any suitable means, including parenteral, subcutaneous, intrapulmonary, and intranasal administration, and if desired for local immunosuppressive treatment, intralesional administration (including perfusing or otherwise contacting the graft with the immunosuppressive agent prior to transplantation). Parenteral infusions include intramuscular, intravenous, intraarterial, or intraperitoneal administration. In addition, the immunosuppressive agent is suitably administered by pulse infusion, particularly with declining doses of the immunosuppressive agent. Preferably, the dosing is given by injections, most preferably intravenous or subcutaneous injections, depending in part on whether the administration is brief or chronic.

The above disclosure generally describes the present invention. A more complete understanding can be obtained by reference to the following specific examples which are provided herein for purposes of illustration only and are not intended to limit the scope of the invention.

EXAMPLE 1

MOLECULAR ENGINEERING OF COLLAGEN-TARGETED VEGF-CBD FUSION PROTEINS

Construction of the VEGF-CBD Fusion Proteins: VEGF is actually a family of 4 isoforms (VEGF-206, 189, 165 and 121) produced by alternative splicing of a single gene (Ferrara et al., Endocrine Rev. 18:4, 1997, Neufeld et a., *Prog. Growth Factor Res.* 5:89–97, 1994; Tischer et al., J. Biol. Chem. 266:11947, 1991). VEGF165, the most abundantly expressed isoform, is a heparin binding glycoprotein exhibiting a single glycosylation site, and is secreted as a homodimer of approximately 45 kDa. VEGF165 can be enzymatically cleaved by plasmin, which removes the carboxyl-terminal heparin-binding region (111–165) to yield the VEGF110 dimer that is equipotent to VEGF120 with respect to mitogenic activity on endothelial cells (Houck et al., *J. Biol. Chem.* 267:26301–26307, 1992). VEGF165-CBD and VEGF110-CBD fusion proteins, as well as the VEGF110 isoform were cloned into constructs suitable for high level expression in *E. coli*. A strategically modified collagen-binding sequence derived from a functional domain within bovine von Willebrand factor (vWF; CBD) involved in the recognition of exposed vascular collagen (Takagi et al., supra, 1992; Tuan et al., supra, 1996) was utilized. A cysteine residue within the original vWF sequence was replaced conservatively by a methionine, in order that this auxiliary domain would not interfere with the elaborate disulfide bond formation required for the folding and/or renaturation of the recombinant growth factor. Flanking linkers were designed to include glycine residues to increase rotational flexibility and to minimize stearic hindrances, while a histidine residue was included to promote an external conformation of the collagen binding domain. Thus, the VEGF-CBD fusion constructs, which incorporate the collagen binding decapeptide WREPSF-MALS (SEQ ID NO:1) into the VEGF protein, was designed for targeting VEGF to collagen exposed by injury, inflammation, disease, or reparative surgical procedures.

The development of these genetically engineered vascular endothelial cell growth factors can be described as the completion of six individual steps as follows:

1) Design of the molecular constructs;
2) Molecular cloning of the expression plasmids;
3) Expression of the recombinant fusion proteins;
4) Purification of the fusion proteins;
5) Renaturation of the recombinant growth factors;
6) Assay of specific biological activities Design and Molecular Cloning of the Recombinant VEGF-CBD Fusion Proteins: A prokaryotic expression vector was engineered to produce tripartite fusion proteins (see FIG. 1: Targeted Congeners of Vascular Endothelial Cell Growth Factor) consisting of a 6×His purification tag, an auxiliary von Willebrand factor-derived collagen-binding domain, and the cDNA sequence encoding the mature active fragment of human VEGF110 (VEGF110-CBD) or VEGF165 (VEGF165-CBD).

The PCR primers utilized in these experiments were as follows:

VEGF-110:
    1. Sense (VEGF-110TS1, 21924)
        CATATGGGTGCACCCATGGCAGAAGGAG (SEQ ID NO:2)
    2. Antisense (VEGF-110AS1, 21926)
        TCATCTATCTTTCTTTGGTCTGCATTC (SEQ ID NO:3)

VEGF-110+CBD
    1. Sense (VEGF-110TS2, 21927)
        CATATGTGGCGCGAACCGAGCTTCATGGCT (SEQ ID NO:4)
        CTGAGCGGTGCACCCATGGCAGAAGGAG (SEQ ID NO:5)
    2. Antisense (VEGF-110AS1, 21926)
        TCATCTATCTTTCTTTGGTCTGCATTC (SEQ ID NO:6)

VEGF-165+CBD
    1. Sense (VEGF-110CTS2, 21927)
        CATATGTGGCGCGAACCGAGCTTCATGGCT (SEQ ID NO:4)
        CTGAGCGGTGCACCCATGGCAGAAGGAG (SEQ ID NO:5)
    2. Antisense (VEGF-165 CBD AS1)
        TCACCGCCTCGGCTTGTCACATCA (SEQ ID NO:7)

| VEGF Sequence Source: | EMBL/GenBank/DDBJ databases Accession number X62568 VEGF Gene, human, bases 1 to 649 |
|---|---|

EXAMPLE 2

EXPRESSION, PURIFICATION AND RENATURATION OF THE VEGF FUSION PROTEINS

The molecular constructs were generated from human endothelial cells by RT-PCR. PCR products were initially ligated into TA cloning vectors, and sequences were confirmed by direct DNA sequencing. Upon confirmation of the correct DNA sequences, the respective inserts were released by enzymatic digestion and cloned into a pET expression vector (Novagen), transformed into competent cells (BL21 DE3 strain of *E. coli*) and protein expression was initiated in the presence of IPTG. The expressed fusion proteins were isolated from *E. coli* inclusion bodies, solubilized with 6M guanidinium HCl, purified to homogeneity under denaturing conditions (8M urea) using nickel chelate chromatography, 8M urea, and renatured by oxidative refolding under optimized redox conditions. The VEGF110 protein is produced in high levels (recovery is ~8 to 10 mg/100 ml bacterial culture) and purified to near homogeneity by metal chelate chromatography, as determined by SDS-PAGE. Initially expressed as an insoluble refractile protein found primarily within the bacterial inclusion bodies, the VEGF110 monomer (~15 kDa) can be solubilized by 6M guanidinium HCl or 8M urea, respectively, and renatured under carefully controlled redox conditions to yield a soluble, renatured dimer that migrates at approximately 33 kDa under nonreducing conditions. Under optimal conditions, approximately 90% of the purified recombinant protein can be renatured and recovered as a dimer.

Figure 2:
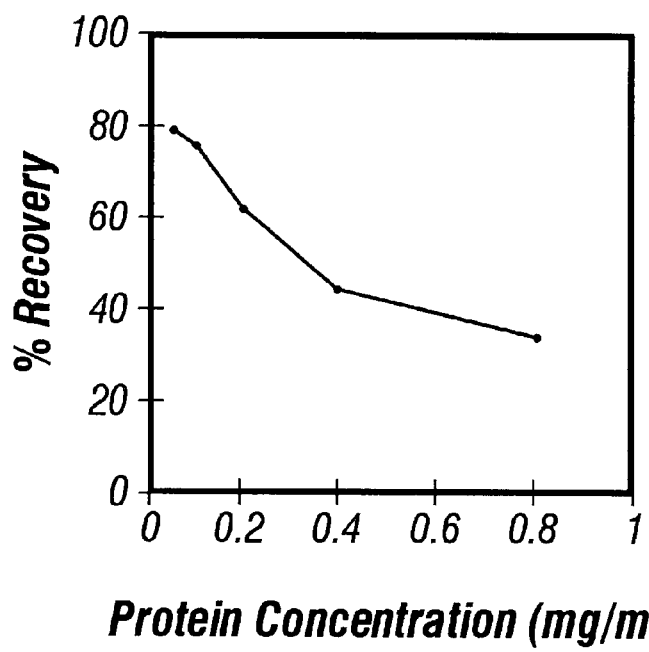
FIG. 2 is a graph documenting the recovery of collagen targeted VEGF proteins.
Figure 3:
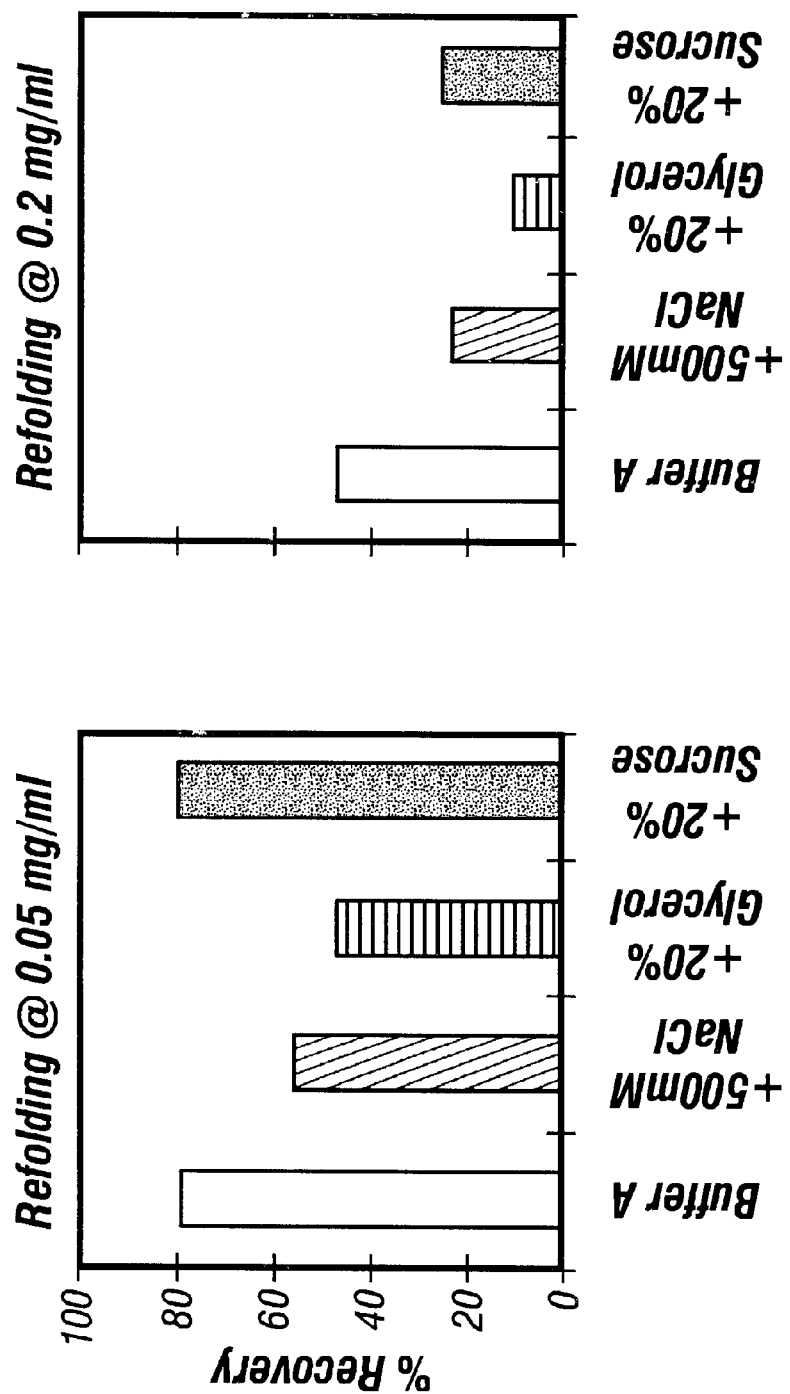
FIG. 3 is a bar graph illustrating the recovery of collagen targeted VEGF proteins in different preparations.

Further studies examined the physicochemical conditions of protein renaturation, including the yield (% recovery) of renatured protein at various protein concentrations (see FIG. 2) and the stabilizing effects (% recovery) of additives (such as sucrose) observed upon withdrawal (dialysis) of the denaturants (see FIG. 3). These studies determined that optimal protein refolding and recovery is observed at protein concentrations below 0.1 mg/ml.

EXAMPLE 3

ASSESSMENT OF SPECIFIC BIOLOGICAL ACTIVITY

Figure 4:
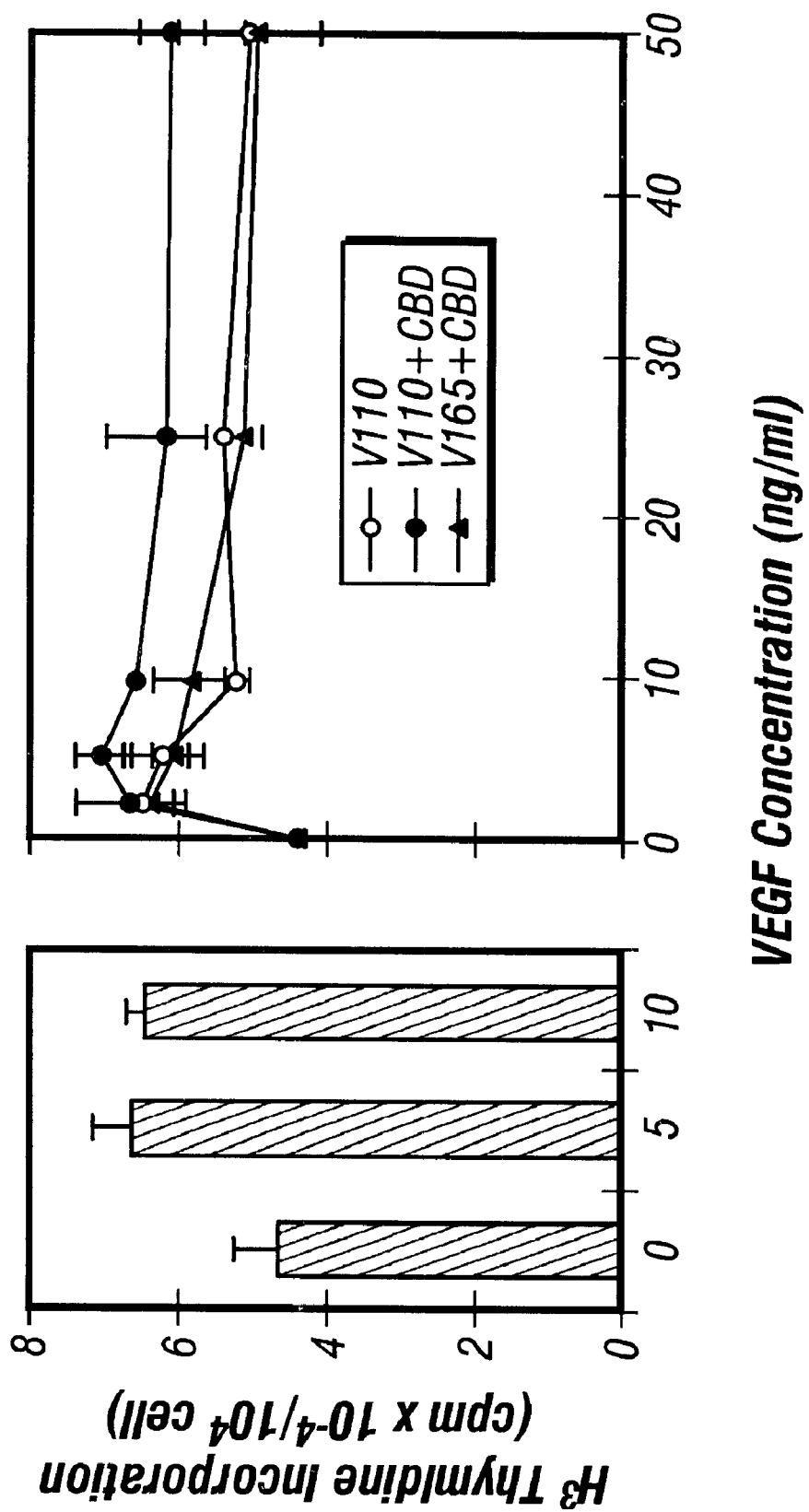
FIG. 4 illustrates the cell proliferation induced by collagen target VEGF proteins. Panel A shows a bar graph illustrating $^3$H-thymidine incorporation induced by different concentrations of a collagen targeted VEGF protein. Panel B shows a graph comparing $^3$H-thymidine incorporation of cells contacted with different concentrations of either V110, V110-CBD, or V165-CBD.
Figure 5:
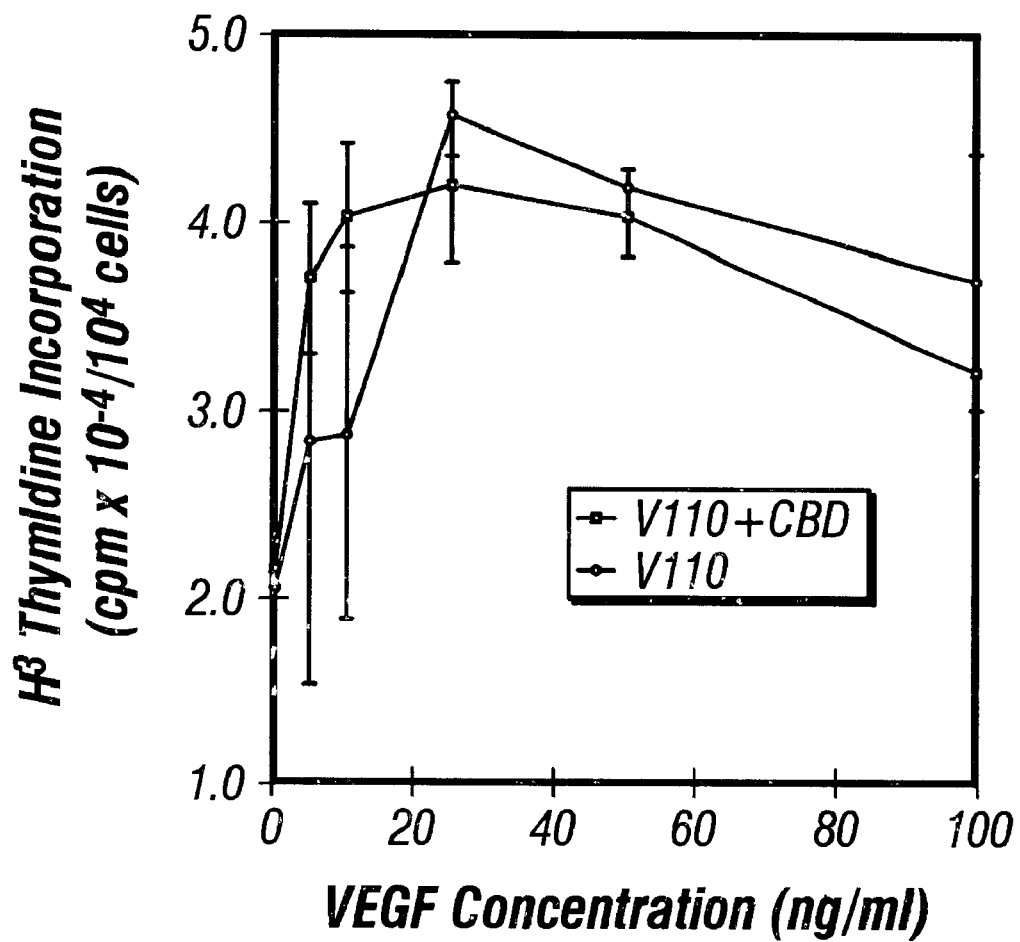
FIG. 5 is a graph comparing the $^3$H-thymidine incorporation induced in cells contacted with different concentrations of V110-CBD and V110.

The biological activity of the recombinant VEGF fusion proteins was evaluated by in vitro cell proliferation assays, using purified commercial VEGF as a standardized control. A spontaneously transformed line of human umbilical cord endothelial cells was obtained from ATCC (ECV304; ATCC CRL-1998) and maintained as monolayers for these assays. VEGF activity was determined by the stimulation of $^3$H-thymidine incorporation observed at (t=16–20 hours) after preculturing the cells for 48 hours under low serum (1%) conditions. Under these conditions, we observed significant stimulation of $^3$H-thymidine incorporation with commercial VEGF concentrations as low as 2.5 ng/ml, with maximal stimulation observed at ~5 ng/ml. As shown in FIGS. 4 and 5, the specific biological activity of each construct (VEGF110, VEGF110-CBD, VEGF165-CBD) was found to be nearly equivalent to that of the commercial standard, indicating that the renatured VEGF fusion proteins were not only refolded into stable dimers, but were demonstrably biologically active.

EXAMPLE 4

ENDOTHELIAL CELL TRAPPING IN SYNTHETIC GRAFTS

Angiogenic factors such as VEGF and CYR61 are known to promote the migration, as well as the proliferation, of endothelial cells. Thus, the binding and concentration of such growth factors onto collagen-coated or gelatin-coated vascular grafts, by virtue of a collagen binding domain genetically engineered into the recombinant growth factor, would serve to fortify the graft and promote endothelialization of the graft in vitro and in vivo.

In addition, the collagen-bound angiogenic factors would presumably serve to recruit endothelial precursor cells that are present in the circulation (Asahara, T. et al., *Isolation of putative progenitor endothelial cells for angiogenesis*, Science 275:964–967, 1997). Moreover, we have previously demonstrated that collagen-bound TGFβ1, in serving as a survival factor for mesenchymal precursor cells, may be used to "capture" stem cells in vitro by selective survival under serum-impoverished conditions for potential use in ex vivo gene therapy protocols (Gordon et al., *Capture and expansion of bone marrow-derived mesenchymal progenitor cells with a transforming growth factor β1-von Willibrand factor fusion protein for retrovirus-mediated delivery of coagulation factor IX*, Human Gene Ther. 8:1835–1394, 1997). Likewise, the collagen bound VEGF fusion proteins may be used in similar manner to select and/or "capture" endothelial stem cells (which express VEGF receptors) for use in ex vivo gene therapy protocols or in cell-based transplantation protocols.

Additionally, we have demonstrated binding of VEG-165+CBD (collagen binding domain) and VEGF110+CBD to injured rat carotid arteries but not to control, non-injured arteries. In contrast, VEGF110 without CBD did not bind to either injured nor non-injured arteries. These experiments were performed in vivo in a rat carotid injury model of vascular restenosis (Zhu et al., Circulation 96(2):628–635, 1997).

Figure 6:
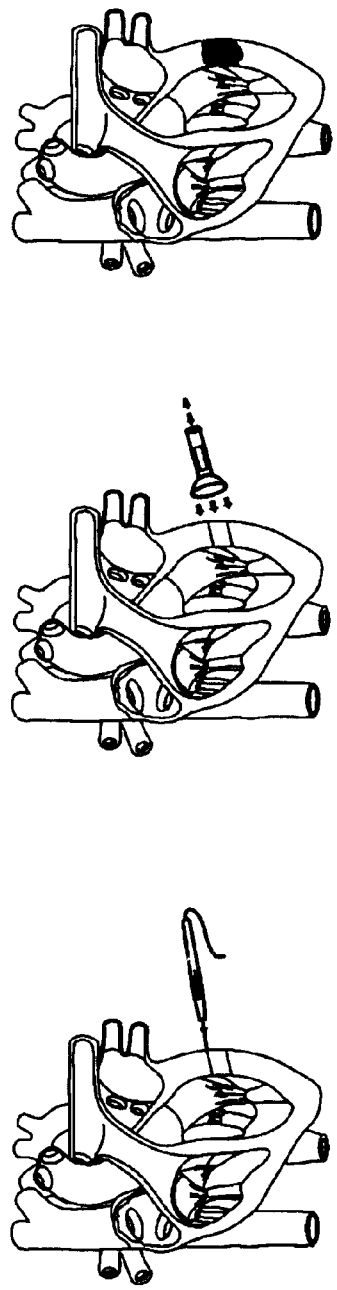
FIG. 6 is a schematic diagram illustrating the augmentation of transmyocardial laser revascularization by CBD-growth factors.

FIG. 6 is a schematic diagram illustrating the augmentation of transmyocardial laser revascularization by CBD-growth factors.

Figure 7:
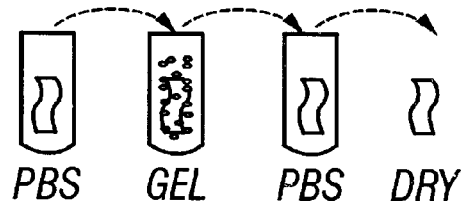
FIG. 7 is a schematic diagram of endothelial cell trapping in synthetic vascular grafts treated with a CBD-growth factor.
Figure 7:
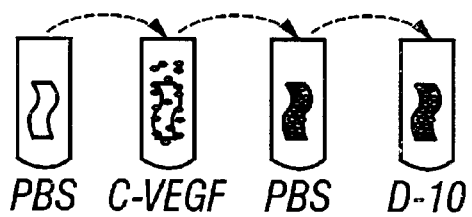
Figure 7:
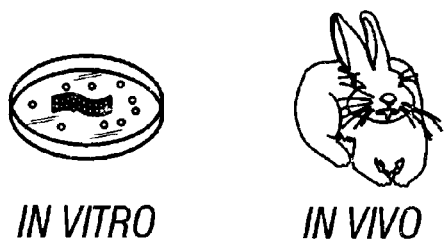
Figure 8:
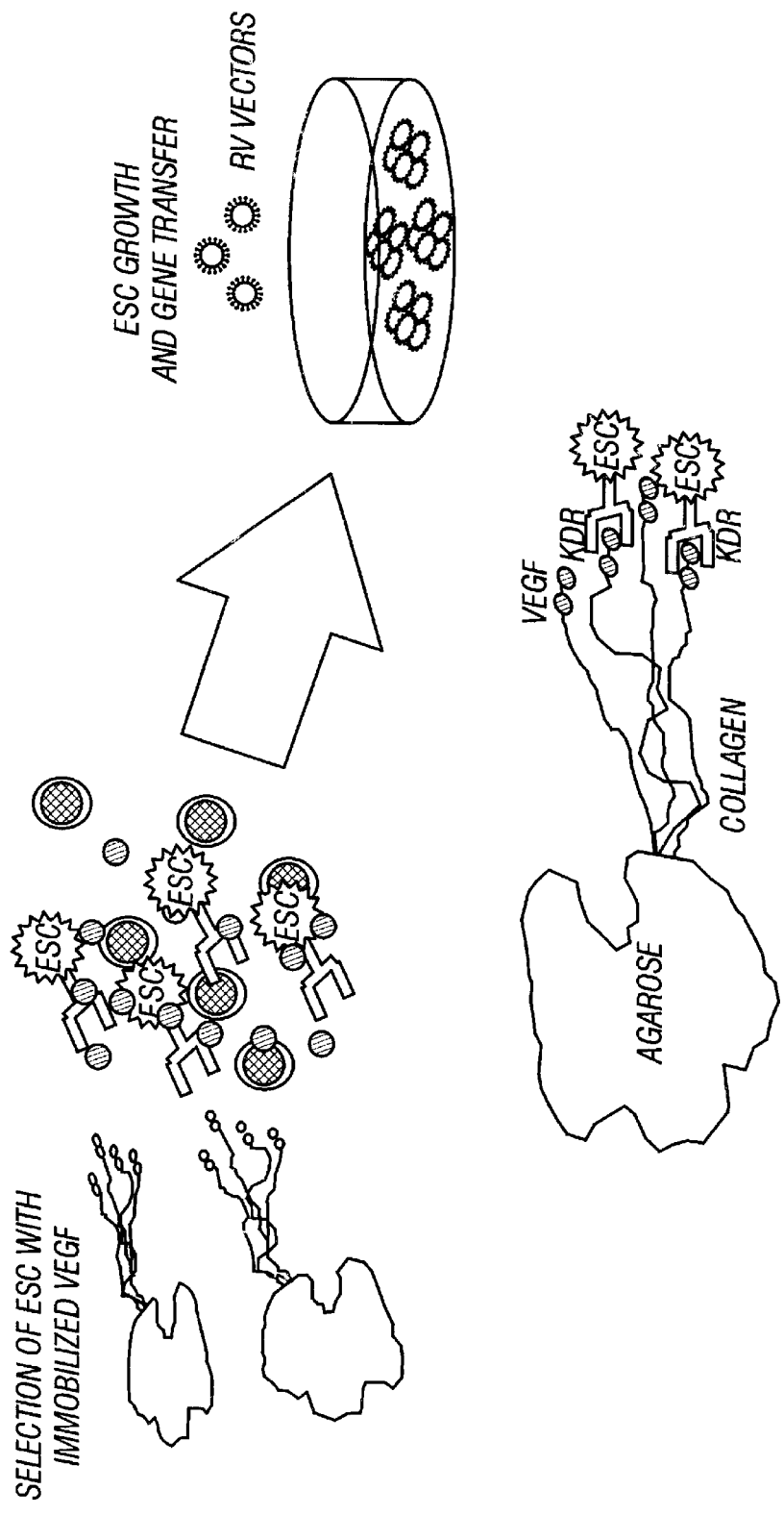
FIG. 8 is a schematic diagram of capture of endothelial stem cells for transplantation and ex vivo gene therapy.

FIG. 7 is a schematic diagram of endothelial cell trapping in synthetic vascular grafts treated with a CBD-growth factor. Although the invention has been described with reference to the presently preferred embodiments, it should be understood that various modifications can be made without departing from the spirit of the invention. Accordingly, the invention is limited only by the following claims.

What is claimed is:

1. A fusion polypeptide comprising:
   a) a collagen binding domain which binds exposed vascular collagen; and
   b) an angiogenesis modulating domain, wherein said angiogenesis modulating domain directly effects endothelial cell proliferation.

2. The fusion polypeptide of claim 1, wherein said collagen binding domain is a collagen binding domain of von Willebrand factor, or conservative variation thereof which retains collagen binding activity.

3. The fusion polypeptide of claim 2, wherein said collagen binding domain comprises the decapeptide Trp-Arg-Glu-Pro-Ser-Phe-Met-Ala-Leu-Ser (SEQ ID NO:1).

4. The fusion polypeptide of claim 1, wherein said angiogenesis modulating domain is selected from the group consisting of a growth factor, growth factor (EGF), hepatocyte growth factor (HGF), platelet derived endothelial cell growth factor (PD-ECGF), platelet derived growth factor (PDGF); insulin-like growth factor (IGF), interleukin-8, growth hormone, angiopoietin, acidic and basic fibroblast growth factors (FGFs), transforming growth factor alpha (TGF-α), vascular endothelial growth factor (VEGF) an enzyme, an enzymatic inhibitor, and an antibody.

* * * * *